(12) United States Patent
Malthe-Sorenssen et al.

(10) Patent No.: US 6,274,762 B1
(45) Date of Patent: Aug. 14, 2001

(54) PREPARATION OF TRI-IODO BENZENE COMPOUNDS

(75) Inventors: Dick Malthe-Sorenssen; Ole Magne Homestad; Britt Sterud, all of Spangereid (NR)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/432,632

(22) Filed: Nov. 12, 1999

Related U.S. Application Data

(63) Continuation of application No. PCT/GB98/01488, filed on May 22, 1998.
(60) Provisional application No. 60/049,175, filed on Jun. 10, 1997.

(30) Foreign Application Priority Data

May 23, 1997 (GB) .................................................. 9710725

(51) Int. Cl.$^7$ ...................... C07C 229/38; C07C 229/62; C07C 237/32
(52) U.S. Cl. .......................... 562/449; 562/450; 562/456; 564/156
(58) Field of Search .................................. 562/456, 449, 562/450; 564/156

(56) References Cited

U.S. PATENT DOCUMENTS

| 3,145,197 | * | 8/1964 | Hoey | 562/456 X |
|---|---|---|---|---|
| 3,991,105 | * | 11/1976 | Wille | 562/456 |
| 4,160,015 | * | 7/1979 | Wiegert | 424/5 |

FOREIGN PATENT DOCUMENTS

| 2033525 | * | 1/1971 | (DE) . |
|---|---|---|---|
| 27 26 196 | | 12/1977 | (DE) . |
| WO 88 08417 | | 11/1988 | (WO) . |
| WO 89 09766 | | 10/1989 | (WO) . |
| WO 91 01296 | | 2/1991 | (WO) . |

\* cited by examiner

*Primary Examiner*—Floyd D. Higel
(74) *Attorney, Agent, or Firm*—Bacon & Thomas

(57) ABSTRACT

The invention provides an improved process for the preparation of a compound containing a 2,4,6-triiodinated benzene ring, said process comprising reacting a 2,4,6-unsubstituted 5-amino-benzoic acid or derivative there of with an iodine halide iodinating agent in an aqueous reaction medium, characterised in that the iodinating agent is added to an aqueous medium containing the 5-amino-benzoic acid or derivative at two different temperature ranges: (A) one or more primary portions of the agent are added at a temperature in the range 40 to 70° C. and then one or more secondary portions of the agent are added at a temperature in the range 75 to 95° C. or (B) one or more primary portions of the agent are added at a temperature in the range 75 to 95° C. and then one or more secondary portions of the agent are added at a temperature of 60 to 70° C.

19 Claims, No Drawings

PREPARATION OF TRI-IODO BENZENE COMPOUNDS

This application is a continuation of pending international application number PCT/GB98/01488 filed May 22, 1998 (of which the entire disclosure of the pending, prior application is hereby incorporated by reference), which itself is a continuation-in-part of U.S. provisional application number 60/049,175 filed Jun. 10, 1997, benefit of which is claimed under 35 U.S.C. 119(e).

The invention relates to processes for the preparation of iodinated X-ray contrast agents and in particular key intermediates therefor, especially 2,4,6-triiodo-5-amino-N,N'-bis (2,3-dihydroxypropyl)-isophthalamide.

The use in X-ray imaging, eg. CT imaging, of iodinated compounds as contrast agents is well established. Such compounds generally contain one or two triiodinated benzene rings and examples of such compounds include iohexol, iopentol, iodixanol, iopamidol and ioversol. The compounds containing a single iodinated benzene ring are commonly referred to as monomers whereas those containing two iodinated benzene rings are referred to as dimers.

In order that the iodinated contrast agents should be water-soluble, the benzene ring is further substituted by solubilizing groups, eg. carboxyl groups, hydroxylated N or C substituted amide groups, or hydroxyalkyl groups.

The industrial manufacture of these iodinated contrast agents involves production of the chemical drug substance followed by formulation to the drug product. The drug substance is usually made in a multistep synthesis and then thoroughly purified before the formulation. In each synthetic step it is important to optimize the yield and minimize the production of impurities and in steps in which expensive reagents are used it is particularly important to optimize usage of those reagents. The iodination reagents are expensive and thus the triiodination of the aromatic ring is an important step which is generally performed at a late stage in the overall synthesis. In this step it is especially important to obtain a high yield with few impurities and minimal wastage of the iodination agent.

For several iodinated contrast agents the iodination step involves reaction of a 2,4,6-unsubstituted 5-amino-benzoic acid or derivative thereof (a "5-AB") with an iododichloride salt, eg. sodium iodine chloride ($NaICl_2$), in an aqueous medium to produce a 2,4,6-triiodo-5-AB.

In accordance with U.S. Pat. No. 3,145,197 (Hoey), the 5-AB is typically triiodinated by reaction with a significant excess of an iododichloride salt in an aqueous hydrochloric acid solution. In this procedure, the 5-AB is charged into the aqueous reaction medium and the iodinating agent is then added in one or two batches.

In WO89/09766 and WO91/01296 (Mallinckrodt) has described an iodination process in which a pre-prepared solution of an AB and a pre-prepared solution of an iodinating agent should be simultaneously added to a hot (74–85° C.) reaction medium in portions spread over a period of hours. In the processes described, there are over twelve additions of portions of the 5-AB and iodinating agent solutions.

The Mallinckrodt patent applications thus essentially teach away from any gradual addition of the iodinating agent to the 5-AB and teach instead that 5-AB and iodinating agent should together be gradually added to the reaction mixture.

We have now found that wastage of the iodinating agent can be reduced, yield of the triiodinated-AB can be optimized and a low impurity profile, particularly in relation to the azo compounds of the triiodinated product, can be obtained if the iodinating agent is added in two or more portions to a reaction medium containing the AB and the temperature of the reaction medium is changed, and preferably increased, during the iodination.

Thus the invention provides a process for the preparation of a compound containing a 2,4,6-triiodinated benzene ring, said process comprising reacting a 2,4,6-unsubstituted 5-amino-benzoic acid or derivative thereof with an iodine halide iodinating agent in an aqueous reaction medium, characterised in that the iodinating agent is added to an aqueous medium containing the 5-amino-benzoic acid or derivative at two different temperature ranges: (A) one or more primary portions of the agent are added at a temperature in the range 40 to 70° C. and then one or more secondary portions of the agent are added at a temperature in the range 75 to 95° C. or (B) one or more primary portions of the agent are added at a temperature in the range 75 to 95° C. and then one or more secondary portions of the agent are added at a temperature of 60 to 70° C.

Process variant (A) is generally preferred, with the iodinating agent used first at the lower temperature and then at the higher temperature. It is also preferred that at least two portions of the agent are added in the first (primary) addition stage, although a single portion may be used if desired. Thus the iodinating agent is preferably added in at least two primary portions to an aqueous medium containing the 5-amino-benzoic acid or derivative at a temperature in the range 40 to 70° C., in that the temperature of the aqueous medium is raised to within the range 75 to 95° C. and in that said iodinating agent is added in at least one secondary portion to the reaction medium while the reaction medium is at a temperature in the range 75 to 95° C. The invention will mainly be described in detail below with regard to this preferred process.

The 5-AB used in the process of the invention is preferably a 5-amino-benzamide, particularly preferably a 5-amino-benzamide which is alkylated at the amide nitrogen, preferably by a $C_{1-6}$ straight chain or branched alkyl group, particularly a hydroxylated alkyl group, eg. a group containing up to 6 hydroxyl groups especially a group containing 2, 3 or 4 hydroxyl groups, eg. a 2-hydroxyethyl, 2,3-dihydroxypropyl, 1,3-dihydroxyprop-2-yl, hydroxymethyl, 1,3-dihydroxy-2 hydroxymethyl-prop-2-yl, 2,3,4-trihydroxybutyl or 1,3,4-trihydroxybut-2-yl group. More particularly preferably the 5-AB is a 5-amino-isophthalamide and especially preferably both amide nitrogens are substituted as discussed above for the benzamide amide nitrogen. Alternatively the 5-AB used may be a 5-amino-N-alkyl-isophthalamic acid or a salt or ester thereof, preferably a compound in which the N-alkyl group is as discussed above for the 5-amino-benzamides.

Especially preferably the 5-AB is 5-amino-N,N'bis(2,3-dihydroxypropyl)-isophthalamide, a key intermediate in the production of iohexol as described in SE 7706792-4 (Nyegaard).

The 5-AB is preferably used in an initial concentration of 0.10 to 0.27 kg/L especially 0.18 to 0.25 kg/L, more especially 0.20 to 0.23 kg/L.

The iodine halide iodinating agent used in the process of the invention is iodine chloride or another iodine halide. This may be produced by adding molecular iodine and another molecular halogen to an alkali metal halide solution, eg. adding $I_2$ and $Cl_2$ to a NaCl or KCl solution. Preparation of $KICl_2$ and $NaICl_2$ in this way is a well established procedure. In the discussion below, iodine chloride will generally be referred to since this is the preferred iodine halide. Nonetheless other iodine halides may be used and the discussion is equally applicable to such other iodine halides.

In the process of the invention, the portions of iodine chloride are preferably 30 to 55% w/w, especially preferably 45–52% w/w, particularly about 50% w/w aqueous solutions, the percentages referring to ICl content. The portions may have different concentrations but conveniently all will have substantially the same ICl concentration, preferably about 50% w/w.

In the preferred method of carrying out the process, the primary portions will preferably be 2 to 6, more preferably 3, portions in total. After the first portion, which preferably corresponds to 1.0 to 2.5 equivalents, particularly 1.1 to 2.0 equivalents and especially 1.2 to 1.45 equivalents, of the 5-AB, the subsequent primary portions are preferably added when the remaining quantity of iodine chloride in the reaction mixture is in the range 0.05 to 1.0% w/w, preferably 0.075 to 0.5% w/w and especially 0.1 to 0.4% w/w. Subsequent primary portions preferably contain approximately equal quantities of iodine chloride. The total iodine chloride addition in the primary portions is preferably 2.05 to 2.85, more preferably 2.3 to 2.8, equivalents of the initial 5-AB. By one equivalent is meant a molar ratio of 1:3 of iodine chloride to iodination sites of which there are three (positions 2, 4 and 6) on the 5-AB.

The secondary portions should be sufficient to raise the total amount of iodine chloride added to 3.05 to 3.20 equivalents, and preferably involve the addition in the secondary portions of a total of 0.2 to 0.90 equivalents of iodine chloride. A single secondary portion is preferred although multiple, eg. 2 or 3, portions may be used. The secondary portion (or portions) is preferably added when the iodine chloride content of the reaction mixture is in the range 0.05 to 0.5 or 0.7%, especially 0.1 to 0.4% w/w. In cases where more than one secondary portion is added, then addition of subsequent secondary portions should preferably be when the iodine chloride content of the reaction mixture is in the range 0.1 to 1.2% w/w, especially 0.4 to 0.75% w/w.

The amount of iodine chloride added in the secondary portions should be minimized in order to minimize formation of the triiodinated azo impurity.

Preferably the iodine chloride is added in four portions (three primary and one secondary).

In this way the quantity of ICl used and unwanted oxidized derivatives of the starting material are minimized.

The portions will generally each be added over a period of 3 to 10 minutes depending on the quantity being added.

For the addition of the initial primary portion, the pH of the reaction mixture to which it is added is generally adjusted to 2.0 to 4.0, preferably 2.0 to 3.5 and more preferably about 3.0, eg by addition of sodium hydroxide. For subsequent portions the pH is preferably adjusted by addition of base to 1.5 to 3.0, preferably 1.5 to 2.5 and more preferably about 2. During the reaction the pH will vary, eg. from 3 to 0 or even −1 from the beginning to the end point after each portion addition.

For the addition of the primary portions of iodine chloride, the temperature of the medium is maintained in the range 40 to 70° C., preferably 50 to 70° C. and more preferably 55 to 65° C., especially about 65° C. In some cases, the preferred range is 40 to 50° C., especially 50 to 60° C., e.g. 50 to 55° C. Optionally the temperature may be increased gradually during this stage, eg. from 40 or 50 to 70° C.

During addition of the secondary portions the temperature of the reaction medium is maintained in the range 75 to 90 or 95° C., preferably 78 to 85° C. Again the temperature may be increased gradually during this stage, eg. from 75 to 90 or 95° C.

Between the primary and secondary portions the temperature of the reaction mixture is increased to a temperature in the range 75 to 90 or 95° C. This may be part of a gradual ramping of the reaction mixture temperature or may represent a single temperature increasing step. Preferably the temperature is increased between primary and secondary portion addition over a period of 20 to 90 minutes, especially 40 to 70 minutes.

After the final portion of iodine chloride is added the reaction is allowed to proceed until the remaining iodine chloride content of the reaction medium is generally in the range 0.2 to 1.20 w/w, preferably 0.30 to 0.90% w/w, especially 0.40 to 0.75% w/w. Overall reaction time from the addition of the first primary portion to the end of the reaction will generally be in the range 6 to 20 hours, preferably about 8 to 14 hours.

When using process variant (B) about 80% of the iodinating agent may be added at the first higher temperature range (in one or more portions) and about 20% at the second lower temperature range, again in one or more portions.

The reaction is quenched by addition of a reducing agent (eg. sodium bisulphite or sodium dithionite) to remove oxidized by-products. After precipitation, the 2,4,6-triiodinated product is then collected and optionally purified before being used further, eg. in an acylation reaction to introduce an optionally hydroxylated $C_{1-6}$-alkyl-carbonyl group at the 5-amino nitrogen or a coupling reaction to produce a dimeric product.

Processes which take the 2,4,6-triiodinated product of iodination and react these further, eg. to produce a chemical drug substance, are deemed to fall within the scope of the process of this invention.

Work-up and further reaction such as described above may be effected in a conventional manner well known to those skilled in the art.

During the iodination reaction, the pH, temperature iodine halide content and the contents of the mono-, di- and tri-iodinated products of the reaction mixture should preferably be monitored, either continuously or on a repeated sampling basis, eg. using known spectroscopic or chromatographic techniques. pH or temperature variations may be compensated for by acid or base addition and by heating or cooling. Iodine halide variation will, as discussed above, determine the timing of iodine halide portion addition and termination of the reaction.

The control of the iodination reaction in this way results in a minimal wastage of iodine halide, a yield of the desired crude bisamide derivatives in the range 92–98%, often 95 to 97%, and a low impurity profile, especially as regards the triiodinated azo impurity. 5-Amino-N-alkylisophthalmic acid (or a salt or ester) may give lower yields, e.g. 70–85%.

The invention will now be described further with reference to the following examples:

EXAMPLE 1

73.7 g of 5-amino-N,N'-bis(2,3-dihydroxypropyl)-isophthalamide was dissolved in 365 ml of water. The pH was adjusted to about 3 by caustic. 90 g of ICl, 50.9% was added to the solution at 60–65° C. and kept at this temperature throughout the reaction. The solution was stirred until the remaining ICl concentration was 0.26%. The pH was adjusted to 2.1 by caustic.

An additional portion of 42.1 g of 50.9% ICl was added and stirred until the remaining ICl concentration was 0.28%. The pH was adjusted to 2.1 by caustic.

An additional portion of 29.3 g of 50.9% ICl was added and stirred until the remaining ICl concentration was 0.36%. The pH was adjusted to 2.2 by caustic.

An additional portion of 34.6 g of 50.9% ICl was added.

The solution was stirred at 75–85° C. until the remaining ICl concentration is 0.58%. The reaction time was approx. 5 hours. The endpoint of the reaction was in addition determined by liquid chromatography. The yield of the crude product was 94%. The level of the azocompound impurity was less than 0.1%.

EXAMPLE 2

73.7 g of 5-amino-N,N'-bis(2,3-dihydroxypropyl)-isophthalamide was dissolved in 365 ml of water. pH was adjusted to 3.1 by caustic. 128.7 g of 50.5% of ICl was added to the solution at 50–60° C. and stirred at the same temperature until the ICl concentration was 0.17%. The pH was adjusted to 2.6 by caustic.

An additional portion of 34.0 g of 50.5% ICl was added and stirred until the remaining ICl concentration was 0.24%. The pH was adjusted to 2.1 by caustic.

An additional portion of 38.8 g of 50.5% ICl was added. The solution was stirred at 80–90° C. until the remaining ICl concentration was 0.47%. The reaction time was approx. 5 hours. The endpoint of the reaction was in addition determined by liquid chromatography. The yield of the crude product was 93%. The level of the azocompound impurity was less than 0.1%.

EXAMPLE 3

73.7 g of 5-amino-N,N'-bis(2,3-dihydroxypropyl)-isophthalamide was dissolved in 365 ml of water. The pH was adjusted to 3.2 by caustic. 81.7 g of ICl, 50.4% was added to the solution at 60–65° C. and kept at this temperature throughout the reaction. The solution was stirred until the remaining IC concentration was 0.22%. The pH was adjusted to 2.0 by caustic.

An additional portion of 42.5 g of 50.4% ICl was added and stirred until the remaining ICl concentration was 0.23%. The pH was adjusted to 2.1 by caustic. An additional portion of 38.6 g of 50.4% ICl was added and stirred until the remaining ICl concentration is 0.42%. The pH was adjusted to 2.2 by caustic.

An additional portion of 42.5 g of 50.4% ICl was added in 2 steps. The first portion, ⅔ of the total was added at 60° C., the remaining when the temperature had reached 80° C. The solution was stirred at 75–85° C. until the remaining ICl concentration was 0.58%. The reaction time was approx. 5 hours. The endpoint of the reaction at this step was in addition determined by liquid chromatography. The yield of the crude product was 95%. The level of the azocompound impurity was less than 0.1%.

EXAMPLE 4

72.5 g of 5-amino-1,3-benzenedicarboxylic acid was suspended in 970 ml of water at ambient temperature. The pH was adjusted to about 1 with hydrochloric acid. 328 g of ICl (48.5%) was added over a period of minutes (40° C.) and maintained for minutes further.

An additional portion of 78.7 g of ICl was added (80° C.). The reaction mixture was kept at this temperature for 4.5 hours. The endpoint of the reaction was determined by liquid chromatography. The reaction mixture was quenched by addition of sodium pyrosulphite.

After cooling to 20° C. the crystalline product was filtered and washed with water. The yield of 5-amino2,4,6-triiodo-1,3-benzenedicarboxylic acid was 77%.

What is claimed is:

1. A process for the preparation of a compound containing a 2,4,6-triiodinated benzene ring, said process comprising reacting a 2,4,6-unsubstituted 5-amino-benzoic acid or a derivative thereof which is a 5-amino-benzamide which is alkylated at the amide nitrogen by one or more straight or branched alkyl groups optionally substituted by one or more hydroxyl groups or said 5-amino-benzamide derivative is a 5-amino-N-alkyl isophthalamide acid or a salt or ester thereof, and wherein the alkyl group at the amide nitrogen is a straight or branched alkyl group optionally substituted by one or more hydroxyl groups; with an iodine halide iodinating agent in an aqueous reaction medium, wherein the iodinating agent is added to an aqueous medium containing the 5-amino-benzoic acid or derivative at two different temperature ranges such that either (A) one or more first portions of the iodinating agent are added at a temperature in the range of 40–70° C. and then one or more second portions of the iodinating agent are added at a temperature in the range of 75–95° C. or (B) one or more first portions of the iodinating agent are added at a temperature in the range of 75–95° C. and then one or more second portions of the iodinating agent are added at a temperature of 60–70° C.

2. A process as claimed in claim 1 in which the iodinating agent is added to an aqueous medium containing the 5-amino-benzoic acid or derivative at a temperature in the range 40 to 70° C., the temperature of the aqueous medium is raised to within the range 75 to 95° C. and said iodinating agent is added in at least one second portion to the reaction medium while the reaction medium is at a temperature in the range 75 to 95° C.

3. A process as claimed in claim 1 in which the iodinating agent is added in at least two first portions to an aqueous medium containing the 5-amino-benzoic acid or derivative at a temperature in the range 40 to 70° C., the temperature of the aqueous medium is raised to within the range 75 to 95° C. and said iodinating agent is added in at least one second portion to the reaction medium while the reaction medium is at a temperature in the range 75 to 95° C.

4. A process as claimed in claim 1 wherein said 5-amino-benzoic acid or derivative is a 5-amino-N,N'bisalkyl-isophthalamide.

5. A process as claimed in claim 4 wherein said 5 amino-benzoic acid or derivative is a 5-amino-N,N'bis (2,3-dihydroxypropyl)-isophthalamide.

6. A process as claimed in claim 1 wherein said iodine halide is iodine chloride.

7. A process as claimed in claim 2 wherein said 5-amino-benzoic acid or derivative is a 5-amino-N,N'bisalkyl-isophthalamide.

8. A process as claimed in claim 7 wherein said 5-amino-benzoic acid or derivative is a 5-amino-N,N'bis(2,3-dihydroxypropyl)-isophthalamide.

9. A process as claimed in claim 3 wherein said 5-amino-benzoic acid or derivative is a 5-amino-N,N'bisalkyl-isophthalamide.

10. A process as claimed in claim 9 wherein said 5-amino-benzoic acid or derivative is a 5-amino-N,N'bis(2,3-dihydroxypropyl)-isophthalamide.

11. A process as claimed in claim 2 wherein said iodine halide is iodine chloride.

12. A process as claimed in claim 3 wherein said iodine halide is iodine chloride.

13. A process as claimed in claim 4 wherein said iodine halide is iodine chloride.

14. A process as claimed in claim 5 wherein said iodine halide is iodine chloride.

15. A process as claimed in claim 1 wherein said iodine halide is iodine chloride.

16. A process as claimed in claim 7 wherein said iodine halide is iodine chloride.

17. A process as claimed in claim 8 wherein said iodine halide is iodine chloride.

18. A process as claimed in claim 9 wherein said iodine halide is iodine chloride.

19. A process as claimed in claim 10 wherein said iodine halide is iodine chloride.

* * * * *